United States Patent [19]

Roy

[11] Patent Number: 5,068,379

[45] Date of Patent: Nov. 26, 1991

[54] METHOD FOR PREPARING SULFONIMIDOYL HALIDES

[75] Inventor: Aroop K. Roy, Midland, Mich.

[73] Assignee: Dow Corning Corporation, Midland, Mich.

[21] Appl. No.: 644,764

[22] Filed: Jan. 23, 1991

[51] Int. Cl.$^5$ ................................................ C07F 7/10
[52] U.S. Cl. ..................................... 556/422; 546/14; 549/4; 549/214
[58] Field of Search ................... 556/422; 549/4, 214; 546/14

[56] References Cited

U.S. PATENT DOCUMENTS 3,637,735  1/1972  Barcza .......................... 556/422 X
3,787,467  1/1974  Lucking et al. ....................... 556/422

OTHER PUBLICATIONS

Levchenko et al., J. Org. Chem. USSR 1, Izsi (1965) and 3,1439 (1967).
Carl Johnson, J.O.C. 44,13 (1979).
T. Bechtold and A. Eingelbrecht of Fluorine Chemistry 19, 379-404 (1982).

Primary Examiner—Paul F. Shaver
Attorney, Agent, or Firm—Robert Spector

[57] ABSTRACT

N-triorganosilylsulfonimidoyl halides are prepared using a novel series of reactions from compounds of hexavalent sulfur selected from amides, chlorides and anhydrides of organosulfonic acids. More specifically, the present method relates to the reaction of an N-triorganosilyl- or an N,N-bis(triorganosilyl)-sulfonamide with a triorganodihalophosphorane to form the corresponding sulfonimidoyl halide.

11 Claims, No Drawings

METHOD FOR PREPARING SULFONIMIDOYL HALIDES

BACKGROUND OF THE INVENTION

1. Field of the Invention

This invention relates to preparing derivatives of organic sulfonimidic acids. More particularly, this invention relates to a novel, convenient method for preparing N-silylated organic sulfonimidoyl halides from the corresponding N-silylated sulfonamides using readily available or easily prepared reactants.

2. Background Information

Organic sulfonimidoyl halides can be represented by the general formula $R^2N=S(O)(R^1)X$, where $R^1$ represents a monovalent substituted or unsubstituted hydrocarbon radical and $R^2$ represents a hydrogen atom or a hydrocarbon radical.

Prior art methods for preparing sulfonimidoyl halides use tetravalent sulfur compounds as starting materials. For example, Levchenko et al. [J. Org. Chem. U.S.S.R. 1, 1251 (1965) and 3, 1439 (1967)] describe the preparation of sulfonimidoyl halides by the reaction of aryl sulfinyl chlorides of the formula ArS(O)Cl with N,N-dichloroalkylamines, their sodium salts or N-chloroamides.

The preparation of alkane sulfonimidoyl halides by the oxidation of the corresponding sulfinamides using chlorine, t-butyl hypochlorite or N-chlorobenzotriazole as oxidizing agents is reported by Carl Johnson [J.O.C. 44, 13 (1979)].

T. Bechtold and A. Eingelbrecht in the Journal of Fluorine Chemistry [19, 379–402 (1982) describe the preparation of N-trimethylsilyl trifluoromethanesulfonimidoyl chloride by the reaction of trimethylsilyl azide with trifluoromethanesulfinyl chloride.

Compounds of tetravalent sulfur useful as reactants for preparing N-silylated sulfonimidoyl halides are not readily available. The sulfinyl chlorides used by Levchenko and Johnson are not suitable for preparing sulfonimidoyl chlorides for a number of reasons, including (1) the alkanesulfinyl chlorides used by Johnson cannot be stored for long periods of time in unvented closed containers because of the danger of pressure build-up resulting from the generation of hydrogen chloride and other gaseous by-products resulting from the decomposition of these compounds that occurs during storage, (2) alkanesulfinyl chlorides have a tendency to decompose by a disproportionation reaction, resulting in formation of the corresponding sulfenyl ($S^{+2}$) and sulfonyl ($S^{+6}$) chlorides, and (3) the arenesulfinyl chlorides used as starting materials by Levchenko et al. have been known to explode during distillation.

The N,N-dihaloamines and amides and the alkali metal haloamides used by Levchenko et al. and the trimethylsilyl azide used by Bechtold et al. are often high energy compounds, requiring extensive safety precautions during their preparation and handling.

Finally, the sulfinamides, t-butyl hypochlorite and N-chlorobenzotriazole used by Johnson are not readily available from commercial suppliers.

An objective of this invention is to provide a method for preparing organic sulfonimidoyl halides and sulfonimidates using initial reactants that do not require preparing or reacting compounds of tetravalent sulfur. In addition, the initial reactants are available from commercial sources, and the initial reactants are stable during long-term storage and pose fewer problems during manipulation and use.

The present inventors discovered a method for preparing N-triorganosilyl organosulfonimidoyl halides by reacting an N-triorganosilyl organosulfonamide or an N,N-bis(triorganosilyl)organosulfonamide of the formula $$R^1SO_2N[Si(R^2)_3]_p(H)_{2-p}$$

where $R^1$ and $R^2$ each represent a monovalent hydrocarbon or substituted hydrocarbon radical and p is 1 or 2, with a triorganodihalophosphorane, $R^3{}_3PX_2$, where $R^3$ represents an aryl radical and X is chlorine or bromine.

The sulfonimidoyl halides, $R^2{}_3SiN=S(O)R^1X$, prepared in accordance with the present method are useful compounds in themselves. A preferred application of these halides is to convert them to the corresponding sulfonimidate by reaction with a phenol or a fluorinated monohydric alcohol. The sulfonimidate can be condensed to form a particularly useful class of polymers referred to as polyorganooxothiazenes or polyorganooxosulfurnitrides.

SUMMARY OF THE INVENTION

This invention provides a method for preparing N-triorganosilylsulfonimidoyl halides by reacting the corresponding N-mono- or N,N-bis(triorganosilyl)sulfonamide with a triaryldihalophosphorane.

DETAILED DESCRIPTION OF THE INVENTION

This invention provides a method for preparing an N-triorganosilylsulfonimidoyl halide represented by the formula $R^2{}_3SiN=S(O)(R^1)X$, said method comprising reacting an N-triorganosilyl sulfonamide corresponding to the formula $R^1SO_2N(H)_n(SiR^2{}_3)_{(2-n)}$ where $R^1$ and $R^2$ are individually selected from the group consisting of monovalent hydrocarbon and monovalent substituted hydrocarbon radicals and n is 0 or 1 with a triaryldihalophosphorane corresponding to the formula $R^3{}_3PX_2$, where $R^3$ represents an aryl radical or a substituted aryl radical and X is chlorine or bromine, to yield said N-triorganosilylsulfonimidoyl halide. The reaction is conveniently conducted at a temperature of from $-78°$ to $40°$ C.

The substituents that can be present on $R^1$ and $R^2$ are limited only by the requirement that these substituents do not react or otherwise interfere with preparation of the final sulfonimidoyl halide in accordance with the present method. The excluded substituents include carbonyl and groups containing labile hydrogen atoms, such as hydroxyl, carboxyl, primary and secondary amino, amido and mercapto (—SH). Preferred substituents include alkoxy and halogen.

Alternatively, the carbon atom bonded to the sulfur atom of the present compounds can be part of a saturated or unsaturated heterocyclic ring structure wherein the hetero atom is oxygen, sulfur or a tertiary nitrogen atom. Representative ring structures include thiophene, pyridine and furan. In a second embodiment the heterocyclic ring can be bonded to sulfur by means of one or more carbon atoms.

The sequence of reactions and the reactants used in the present method will now be discussed in detail.

Preparation of the N-Triorganosilyl and N,N-Bis(Triorganosilyl)sulfonamide

In accordance with the first step of the present method a N-(triorganosilyl)sulfonamide (3) is prepared by reacting 1) the chloride (1), or anhydride (2) of an organosulfonic acid containing the same organic group bonded to sulfur as desired in the final sufonimidoyl halide with a hexaorganodisilazane. Alternatively, the N-triorganosilyl or N,N-bis(triorganosilyl)sulfonamide can be prepared by reaction of the corresponding amide with the combination of a triorganochlorosilane with triethylamine or other suitable tertiary amine to neutralize the hydrogen chloride generated as a by-product of the reaction. This step of the process is depicted in the following equations 1, 2 and 3.

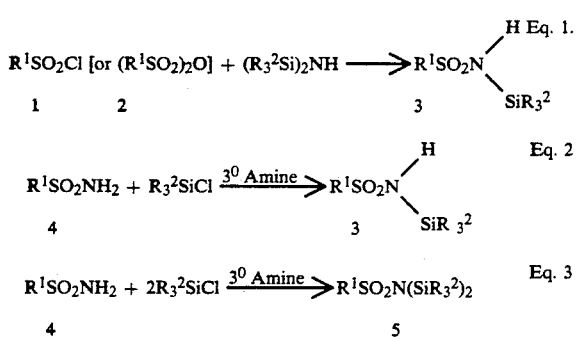

In the formulae of these equations $R^1$ and $R^2$ are individually selected from monovalent hydrocarbon and substituted hydrocarbon radicals as defined in the preceding section of this specification. $R^1$ is preferably alkyl containing from 1 to 20 carbon atoms, halogenated alkyl, aryl, halogenated aryl, aralkyl or aralkenyl. Particularly preferred embodiments of $R^1$ included but are not limited to methyl, 3-chloropropyl, phenyl, p-fluorophenyl, beta-styryl (PhC=CH— where Ph is phenyl) and ethyl. $R^2$ is preferably alkyl containing from 1 to 10 carbon atoms, based on the availability of the intermediates used to prepare these organosilicon compounds.

The monosilyl sulfonamide (3) is converted to the corresponding sulfonimidoyl halide (7) by reacting it with a dihalophosphorane, $R^3_3PX_2$ (6) in the presence of a tertiary amine as an acid acceptor as shown in equation 4. The corresponding disilyl sulfonamide (5) is converted to sulfonimidoyl halide (7) by reaction with the phosphorane (6) as shown in equation 5. No base is required. Instead, an additional equivalent weight of alcohol and base are used in the next step of the present method to convert the chlorosilane by-product to a more innocuous alkoxysilane.

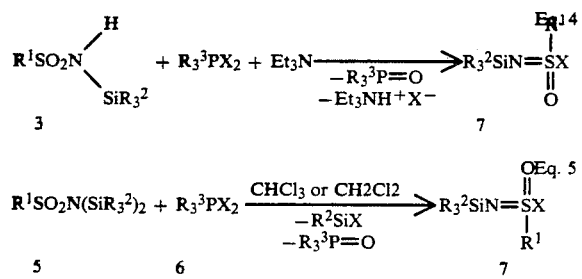

The dihalophosphorane can be prepared as shown in equation 6 by reacting a triarylphosphine $R^3_3P$ with hexachloroethane to yield the dichlorophosphorane, or with elemental bromine to yield the corresponding dibromophosphorane. To ensure a complete reaction, the reaction mixture containing the phosphine and hexachloroethane should be heated at the boiling point for at least four hours. The reaction between the phosphine and bromine is considerably more rapid.

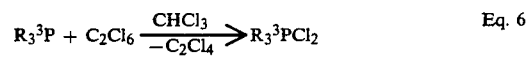

As previously discussed, $R^3$ represents an aryl radical or a substituted aryl radical. The only limitation on the substituent(s) that can be present on $R^3$ is that it not interfere during the subsequent reaction of the phosphorane. $R^3$ preferably represents a phenyl radical.

In accordance with a preferred end use of the present N-silylated sulfonimidoyl halides, these compounds are reacted with an alcohol or phenol $R^4OH$ in the presence of a tertiary amine or other acid acceptor to convert the sulfonimidoyl halide to the corresponding sulfonimidate (8). The reaction is depicted in equation 7, where $R^4$ represents a hydrocarbon or fluorinated hydrocarbon radical. $R^4$ preferably represents a fluorinated alkyl or an aryl radical. This preference is based on the ability of these compounds to undergo a thermally induced condensation to form polyoxothiazenes without rearrangement to the corresponding sulfonamides.

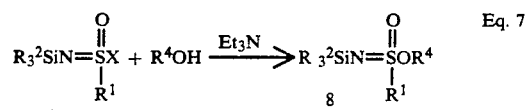

The $R^1$ substituents in preferred compounds are alkyl containing from 1 to about 20 carbon atoms, haloalkyl, phenyl, beta-styryl or halogenated phenyl where the halogen is chlorine, bromine or fluorine.

EXAMPLES

The following examples describe preferred embodiments of the present method and a class of useful polyorganooxothiazenes that are obtained using compounds prepared using the present method as intermediates. The examples should not be interpreted as limiting the scope of the invention defined in the accompanying claims either with respect to the present compounds or their methods of preparation. Unless otherwise indicated all parts and percentages in the examples are by weight.

The parenthetical numbers identifying the intermediates in the examples refer to the numbers directly below the products and reactants in the foregoing equations. Where interpretation of maxima in $^1H$ nuclear magnetic resonance (NMR) spectra are provided s represents a singlet, d represents a doublet, t represents a triplet, q a quadruplet, m a multiplet and the shifts are reported as delta values.

EXAMPLE

This example describes the preparation of sulfonamides from the corresponding sulfonyl halides and their subsequent conversion to sulfonimidates and a useful class of polymers.

Preparation of N- Silyl- and N,N-Disilyl Sulfonamides

Preparation of N,N-bis(trimethylsilyl)Methanesulfonamide (5a)

A glass reactor equipped with a stirrer, nitrogen inlet, reflux condenser and addition funnel was purged with nitrogen and charged with 29.1 g (0.30 mol) of methanesulfonamide, $MeSO_2NH_2$, where Me represents the methyl radical, 84.9 ml (0.605 mol) of triethylamine and 240 ml of dry benzene. Trimethylchlorosilane (129.5 ml, 1.00 mol) was then added through the addition funnel over a period of 15 minutes to the stirred mixture, followed by heating at the boiling point for three hours. The mixture was then diluted with 200 ml of hexane and stirring was continued for 30 minutes.

The solid salt which precipitated during the reaction was washed three times with a total of about 250 ml. of hexane and the washings were combined with the liquid portion of the reaction mixture. The solvents together with unreacted silane and amine were removed from this liquid by distillation using reduced pressure at a temperature of 45° to 55° C. The light brown liquid that remained was distilled twice using a 10 cm Vigreaux column to yield 36.9 g (51% yield) of a colorless liquid that boiled between 100° and 106° C. under a pressure of 5.2 mm Hg.

The reaction product was found to contain 5% of the corresponding N-trimethylsilyl methanesulfonamide.

Preparation of N-trimethylsilyl Methanesulfonamide (3a, R=Me)

A glass reactor equipped with a water-cooled reflux condenser, a stirrer and a nitrogen inlet was purged with nitrogen and charged with hexamethyldisilazane (88.8 ml, 0.4123 mole), and methanesulfonyl chloride (32.2 ml, 0.4082 mole). The mixture was then heated to a temperature of between 90° and 100° C. until initiation of the reaction. The mixture was then heated to between 115° and 120° C. for two hours to maintain refluxing of liquid, at which time it was allowed to cool to room temperature. The trimethylchlorosilane produced as a by-product of the reaction was then removed under reduced pressure.

The crude monosilylsulfonamide (3a), which was greater than 98 percent pure, was either used as such or purified by distillation. The $^1H$ nuclear magnetic resonance (NMR) spectrum of the crude product as a 20–25 percent solution in chloroform using a frequency of 90 MHz. exhibited the following shifts: 0.10 (s, 9H); 2.8 (s, 3H); and 5.25 (s, 1H, NH).

Preparation of N-Trimethylsilyl Benzenesulfonamide (3b, R=Phenyl)

A glass reactor equipped with a reflux condenser, addition funnel and mechanically operated stirrer was purged with nitrogen and charged with benzenesulfonamide (48.12 g., 0.300 mol), triethylamine (44.6 ml, 0.315 mol) and 230 ml of benzene which had been previously freed from water. Chlorotrimethylsilane (38.8 ml, 0.300 mol) was added through the addition funnel to the mixture over 15–20 minutes. The addition funnel was then rinsed with 10 ml of benzene and the mixture heated at the boiling point for three hours.

After cooling to room temperature the mixture was filtered under nitrogen and the solid which had precipitated in the reactor was isolated, washed three times with benzene, and the washings combined with the liquid portion of the mixture. The liquid was then heated at 45°-55° C. under reduced pressure for a period of time sufficient to remove the solvent and excess amine. The residue, a semi-solid, was distilled under a pressure of 0.05 mm Hg. The amount of product obtained was equivalent to a 91% yield of the desired N-trimethylsilyl benzene sulfonamide (3b).

The $^1H$ NMR spectrum of the product (90 MHz, 20–25% in $CH_2Cl_2$) exhibited maxima at the following shift values: 0.18 (s, 9H); 5.25 (s, 1H, NH, using chloroform as the solvent), 7.38–7.61 (m, 3H), 7.75–7.91 (m, 2H).

Preparation of N-Trimethylsilyl 4-Fluorobenzenesulfonamide (3c)

A glass reactor equipped with a stirrer, reflux condenser and gas inlet was charged with solid 4-fluorobenzenesulfonyl chloride (0.250 mol, 49.65 g). Hexamethyldisilazane (0.263 mol, 56.6 ml) was added to the reactor and the mixture was gradually heated with stirring to a temperature of 115° C., at which time it became clear. The mixture was then heated at the boiling point for 21 hours. Analysis of the mixture by $^1H$ NMR indicated that the reaction was about 50% complete. Volatile materials were then removed by heating at a temperature of 65° C. under reduced pressure to yield a brown liquid which was distilled to remove unreacted sulfonyl chloride. The residue was redistilled under a pressure of 0.03 mm. Hg. The fraction collected from 40° to 97° C. was analyzed by $^1H$ NMR and was found to contain the N-mono- and N,N-bis(trimethylsilyl)sulfonamides in a 1:1 molar ratio. Using the same analytical technique a second fraction collected within the range from 97° and 122° C. was found to contain the N-mono- and N,N-bis(trimethylsilyl)sulfonamides in a 8.5:1 molar ratio. The second fraction was used as the starting material (3c) for the subsequent reaction.

Preparation of N-Trimethylsilyl 2-Phenylethylenesulfonamide (3d)

A glass reactor equipped with a mechanically operated stirrer, reflux condenser and gas inlet was charged with 2-phenylethylenesulfonyl chloride (0.2464 mol, 53.6 ml) and hexamethyldisilazane (0.2488 mol, 53.6 ml), following which the contents of the reactor were heated. The generation of chlorotrimethylsilane became evident at a temperature of 107°–110° C., and the mixture was heated for one hour at a temperature of 115°–117° C. Volatile materials were removed by heating to a temperature of 45° to 55° C. under reduced pressure to yield a thick, reddish colored material. This material was distilled twice to yield 42.7 g of N-trimethylsilyl 2-phenylethylenesulfonamide. The product was collected at 155°–160° C. under a pressure of 0.05 mm. Hg. Analysis by $^1H$ NMR indicated that the product was 95% pure. The NMR spectrum obtained using a 20–25% solution of the product in acetonitrile and an RF of 90 MHz exhibited signals corresponding to the following chemical shifts: 0.33 (s, 9H), 5.50 (s, 1H, NH), 7.08 (d, 1H), and 7.40–7.80 (m, 6H).

Preparation of N-trimethylsilyl 3-Chloropropanesulfonamide (3e)

A glass reactor equipped with a stirrer, reflux condenser and gas inlet was charged with hexamethyldisilazane (0.4235 mol, 91.2 ml) and 3-chloropropanesulfonyl chloride (0.4193 mol, 75.0 g). The contents of the reactor were heated. A refluxing liquid was first observed at a temperature of 85°-95° C., and the mixture became clear. The mixture became cloudy at a temperature of about 105 degrees. The temperature of the mixture was maintained at 120° C. for 90 minutes and at 145°-150° C. for 15 minutes. The mixture was then allowed to cool to room temperature, at which time it was filtered, the solids were washed with benzene, and the washing liquid combined with the liquid portion of the mixture. The combined liquids were then heated at 60°-65° C. under reduced pressure to remove volatile materials and then distilled. The fraction boiling from 127°-129° C. under a pressure of from 0.04-0.07 mm. Hg was collected, and was equivalent to a 72.5% yield based on initial reactants. The $^1$H NMR spectrum was consistent with the expected product.

Preparation of N-Trimethylsilyl Ethanesulfonamide (3f)

This product was prepared following the general procedure described for the corresponding 3-chloropropanesulfonamide using ethanesulfonamide as the reactant. The initial mixture was heated at 125°-130° C. for two hours. The product was isolated in the same manner and distilled from 94° to 96° C. under a pressure of 0.65 mm. Hg. The yield was 37%.

General Procedure for Preparation of N-trimethylsilylalkane-and N-trimethylsilylarenesulfonimidoyl Chlorides (7) from the Corresponding N-Trimethylsilylsulfonamides A glass reactor equipped with a stirrer, addition funnel and gas inlet was purged with nitrogen and charged with hexachloroethane as a 1 to 2 molar solution in dry chloroform. A solution of triphenylphosphine as a 1 to 2 molar solution in dry chloroform was added to the reactor with stirring over 5 min. while the reactor was cooled to 0° C. The mixture was heated at the boiling point for 4.5 hr and then cooled to 0° C. Triethylamine was then added to the reactor over 5 minutes at a temperature of 0° C. followed by the addition of a 4 to 7 molar solution of a monosilylsulfonamide in dry chloroform over a 10-15 minute period while the reactor was cooled to −78° C. The contents of the reactor were then allowed to warm to 0° C. during which time the mixture became virtually clear. This was interpreted as indicative of the formation of a sulfonimidoyl chloride. The presence of the sulfonimidoyl chloride was inferred from the $^1$H NMR spectrum of the mixture. In some instances this analysis was performed when a clear mixture was first observed.

Because the sulfonimidoyl chlorides are not stable for extended periods above 0° C., they were not isolated. Instead, they were allowed to react immediately with phenol or trifluoroethanol in the presence of triethylamine to form the corresponding sulfonimidates.

N-trimethylsilylmethanesulfonimidoyl Chloride (7a)

The reactants used in the general procedure were hexachloroethane (0.315 mol, 76.09 g), triphenylphosphine (0.3165 mol, 83.85 g), triethylamine (0.315 mol, 44.6 ml), and N-trimethylsilyl sulfonamide (3a) (0.315 mol, 52.6 g). The $^1$H NMR spectrum (90 MHz, CHCl$_3$ as the solvent) exhibited signals at the following shift values: 0.13 (s, 9H) and 3.45 (s, 3H).

N-trimethylsilylbenzenesulfonimidoyl Chloride (7b)

The reactants used in the general procedure were hexachloroethane (0.1353 mol, 32.68 g), triphenylphosphine (0.1367 mol, 36.22 g), triethylamine (0.1353 mol, 19.2 ml), and N-trimethylsilylsulfonamide (3b) (0.1353 mol, 31.0 g).

N-trimethylsilyl-4-fluorobenzenesulfonimidoyl chloride (7c)

The reactants used in the general procedure were hexachloroethane (0.0953 mol, 23.02 g), triphenylphosphine (0.0963 mol, 25.51 g), triethylamine (0.0991 mol, 12.5 ml), and a mixture of N-mono- and N,N-bis(trimethylsilyl)sulfonamides (3c) and (5c) containing about 89.5% monosilylsulfonamide (3c) (0.0881 mol, 21.76 g).

N-trimethylsilyl-2-phenylethylenesulfonimidoyl Chloride (N-trimethylsilyl-β-styrenesulfonimidoyl Chloride) (7d)

The reactants used in the foregoing general procedure were hexachloroethane (0.1667 mol, 40.27 g), triphenylphosphine (0.1683 mol, 44.59 g), triethylamine (0.1667 mol, 23.6 ml), and the N-trimethylsilyl sulfonamide 3d (0.1667 mol, 42.50 g).

N-trimethylsilyl-3-chloropropanesulfonimidoyl Chloride (7e)

The reactants used in the foregoing general procedure were hexachloroethane (0.0902 mol, 21.79 g), triphenylphosphine (0.0911 mol, 24.14 g), triethylamine (0.0902 mol, 12.8 mL), N-trimethylsilyl sulfonamide (3e) (0.0902 mol, 20.66 g). The identity of the reaction product was confirmed by the presence of signals at the following shifts in the $^1$H NMR spectrum: 90 MHz (CHCl$_3$): 0.05 (s, 9H), 2.12 (m, 2H, SCH$_2$CH$_2$), 3.38 (t, 2H, SCH$_2$), 3.45 (t, 2H, ClCH$_2$).

N-trimethylsilylethanesulfonimidoyl Chloride (7f)

Hexachloroethane (0.1110 mol, 26.81 g), triphenylphosphine (0.1121 mol, 29.70 g), triethylamine (0.1110 mol, 15.7 mL), monosilylsulfonamide (3f) (0.1110 mol, 20.1 g). $^1$H NMR signals (90 MHz, CHCl$_3$): 0.00 (s, 9H), 1.27 (t, 3H), 3.23 (q, 2H).

General Procedure for the Synthesis of N-trimethylsilylalkane-and N-Trimethylsilyl Arenesulfonimidates (8) from the corresponding sulfonimidoyl chlorides (7)

A mixture of the appropriate alcohol (2,2,2-trifluoroethanol or phenol) and an amount of triethylamine based on 98% yield of sulfonimidoyl chloride dissolved in an amount of dry benzene sufficient to form a 3 to 5 molar solution of the amine or alcohol was added over a 15 to 30 minute period with stirring to a glass reactor containing the sulfonimidoyl chloride dissolved in chloroform from the previous reaction. The reactor was maintained at a temperature of 0° C. during the addition. Following completion of the addition the mixture was stirred at 0°-5° C. for 60-120 minutes then diluted with a quantity of isomeric hexanes equivalent to 20-40% of the volume of chloroform present in the mixture and the mixture stirred for about 16 hours at room temperature.

About 70 to 80 percent of the solvents and other volatile materials were then removed under reduced pressure at a temperature of from 40° to 45° C. A quantity of isomeric hexanes sufficient to either provide smooth stirring of the three equivalents of solid by-products or sufficient to form a 0.5-1.0 molar solution of the sulfonimidate, based on theoretical yield, were added. The mixture was stirred for 30-60 minutes, filtered under nitrogen and the solids washed three or four times with hexanes. The washings were combined with the initial filtrate, which was then concentrated at a temperature of 45° to 55° C. under reduced pressure. This usually resulted in the precipitation of additional solid material. Isomeric hexanes was again added, the mixture stirred 15-30 minutes, filtered under nitrogen, and the solids again washed two or three times with hexanes. Solvents were removed from the combined filtrate and washings at a temperature of 45° to 55° C. under reduced pressure to yield the crude N-trimethylsilyl sulfonimidate.

The crude sulfonimidate was purified by distillation under reduced pressure from one to three times to yield the pure N-trimethylsilyl sulfonimidate.

2,2,2-Trifluoroethyl-N-trimethylsilyl Methanesulfonimidate (8aa)

The reactants used in the general procedure were sulfonimidoyl chloride (7a), triethylamine (0.3089 mol, 43.8 ml) and 2,2,2-trifluoroethanol (0.3087 mol, 22.5 ml). The boiling range of the sulfonimidate was 77°-78° C./7.7 mm Hg and the yield was 73%.

$^1$H NMR signals (90 MHz, $C_6H_6$): 0.30 (s, 9H), 2.40 (s, 3H), 3.97 (m, 2H, diastereotopic $OCH_2CF_3$ protons).

Elemental Analysis: Calc. C, 29.14; H, 5.66; N, 5.62; S, 12.86. Found C, 29.01; H, 5.47; N, 5.65; S, 12.96.

Phenyl-N-trimethylsilyl Methanesulfonimidate (8ab)

The reactants used in the general procedure were sulfonimidoyl chloride (7a), triethylamine (0.4657 mol, 66.0 ml) and phenol (0.4655 mol, 43.81 g). Boiling range of the product: 73°-78° C./0.03 mm. Yield 53% after three distillations. $^1$H NMR signals (90 MHz, $CH_2Cl_2$): 0.05 (s, 9H), 3.05 (s, 3H), and 7.08-7.51 (m, 5H).

2,2,2-trifluoroethyl-N-trimethylsilyl Benzenesulfonimidate (8ba)

The reactants used in the general procedure were sulfonimidoyl chloride (7b), triethylamine (0.1377 mol, 19.5 ml), 2,2,2-trifluoroethanol (0.1375 mol, 10.0 ml). Boiling range of product: 84°-86° C./0.7 mm. Yield: 27%. $^1$H NMR signals (90 MHz, $CH_3CN$): 0.27 (s, 9H), 4.35 (q, 2H, multiplet in benzene), 7.63-7.83 (m, 3H), 7.93-8.13 (m, 2H).

Phenyl-N-trimethylsilyl Benzenesulfonimidate (8bb)

The reactants used in the general procedure were sulfonimidoyl chloride (7b), triethylamine (0.1328 mol, 18.8 ml), phenol (0.1326 mol, 12.48 g). Boiling range: 110°-121° C./0.05 mm. Yield: 21% $^1$H NMR signals (90 MHz, $CH_2Cl_2$): 0.21 (s, 9H), 6.78-7.01, 7.11-7.38 (m, 5H), 7.41-7.65 (m, 3H), 7.78-8.01 (m, 2H).

Phenyl-N-trimethylsilyl-4-fluorobenzenesulfonimidate (8cb)

The reactants used in the general procedure were sulfonimidoyl chloride (7c), triethylamine (0.0936 mol, 13.3 ml), phenol (0.0934 mol, 8.79 g). Boiling range of product: 125°-131° C./0.25 mm. Yield: 15%. $^1$H NMR signals (90 MHz, $CH_3CN$): 0.24 (s, 9H), 6.83-7.57 (m, 7H), and 7.83-8.1 (m, 2H).

2,2,2-trifluoroethyl-N-trimethylsilyl-2-phenylethylenesulfonimidate (8da)

The reactants used in the general procedure were sulfonimidoyl chloride (7d), triethylamine (0.1634 mol, 23.2 ml), 2,2,2-trifluoroethanol (0.1633 mol, 11.9 ml). Boiling range of product: 105°-108° C./0.04 mm; Yield: 45%; $^1$H NMR signals (90 MHz, $CH_3CN$): 0.3 (s, 9H), 4.47 (q, 2H, multiplet in benzene), 7.02 (d, 1H), 7.40-7.87 (m, 6H).

Elemental Analysis: Calc. C, 46.27; H, 5.38; N, 4.15; S, 9.50. Found C, 46.80; H, 5.42; N, 4.23; S, 10.51.

Phenyl-N-trimethylsilyl 2-Phenylethylenesulfonimidate (8db)

The reactants used in the general procedure were sulfonimidoyl chloride (7d), triethylamine (0.0853 mol, 12.1 ml), phenol (0.0852 mol, 8.02 g). The $^1$H NMR spectrum of the crude clearly indicated the formation of the desired sulfonimidate in about 55% yield. The product was found to be unstable to distillation, possibly condensing to form a polymer below its boiling point. A similar effect was observed with sulfonimidate 8eb as described below.

2,2,2-trifluoroethyl-N-trimethylsilyl 3-Chloropropanesulfonimidate (8ea)

The reactants used in the general procedure were sulfonimidoyl chloride 7e, triethylamine (0.1444 mol, 20.5 ml), 2,2,2-trifluoroethanol (0.1443 mol, 10.5 ml). Boiling Point: 85°-87° C./1.0 mm. Yield: 67%. $^1$H NMR (90 MHz $C_6H_6$); 0.28 (s, 9H), 1.77-2.14 (m, 2H, $SCH_2CH_2$), 2.86 (t, 2H, $SCH_2$), 3.17 (t, 2H, $ClCH_2$), 4.04 (m, 2H, $OCH_2CF_3$).

Phenyl-N-trimethylsilyl 3-Chloropropanesulfonimidate (8eb)

The reactants used in the general procedure were sulfonimidoyl chloride 7e, triethylamine (0.0884 mol, 12.5 ml), phenol (0.0883 mol, 8.30 g). $^1$H NMR of the crude clearly indicated the formation of the desired sulfonimidate in ca. 66% yield, but the product was found unstable to distillation, rapidly condensing (with the generation of $Me_3SiOPh$) to the corresponding oxothiazene polymer at a temperature of about 100° C. under a pressure of 0.025 mm Hg. $^1$H NMR signals (90 MHz, $CH_2Cl_2$) for the crude sulfonimidate: 0.03 (s, 9H), 2.08-2.58 (m, 2H, $SCH_2CH_2$), 3.35 (t, 2H, $SCH_2$), 3.68 (t, 2H, $ClCH_2$), ca. 7.08-7.48 (m, 5H, $OC_6H_5$). $^1$H NMR signals (90 MHz, $CH_2Cl_2$) for the crude polymer: 2.07-2.67 (broad hump, 2H, $SCH_2CH_2$), 3.27-3.97 (broad hump, 4H, $SCH_2$, $ClCH_2$).

Phenyl-N-trimethylsilyl Ethanesulfonimidate (8fb)

The reactants used in the general procedure were sulfonimidoyl chloride 7f, triethylamine, (0.1089 mol, 15.4 ml), and phenol (0.1087 mol, 10.23 ml).

Boiling range of product: 71°-73° C. at 10.8 mm Hg Yield=24%.

$^1$H NMR signals (90 MHz, $CH_2Cl_2$): 0.01 (s, 9H), 1.38 (t, 3H), 3.15 (q, 2H), and 7.06-7.53 (m, 5H).

General Procedure for Preparation of Poly(methyloxothiazene) by the Thermal Condensation of Sulfonimidates The sulfonimidate was placed in a pre-weighed, heavy-walled glass ampule using a pipette. The ampule contents were degassed using a vacuum line and standard freeze-thaw techniques. This procedure was repeated for a total of three times.

When a solid polymerization catalyst was used the catalyst was transferred into the ampule under a nitrogen atmosphere prior to addition of the sulfonimidate. Liquid catalysts were placed in the ampule using a hypodermic syringe following addition of the sulfonimidate and prior to freezing of the contents of the ampule. In all instances the concentration of catalyst was 0.05 mole percent, based on monomer.

When 2,2,2-trifluoroethyl-(N-trimethylsilyl)methanesulfonimidate was used as the monomer, evacuation of the ampule was performed at room temperature under a pressure of 10 mm Hg prior to dagassing at full vacuum by the freeze-thaw technique.

The ampule was then sealed with the contents frozen and placed in a metal pipe equipped with screw caps. The pipe was then placed in a thermostatically regulated oven maintained at 120° C. for the time period specified in Table 1.

At the end of this period, the pipe was allowed to cool to room temperature. The ampule was taken out, cooled in liquid nitrogen and then opened. The liquid remaining in the ampule was analyzed using $^1$H NMR to determine the amount of monomer that had reacted.

The crude solid polymer in the ampoule was washed three times with methylene chloride and then dried under reduced pressure. The polymer was then dissolved in 4 ml of N,N-dimethylformamide and precipitated by dropwise addition of the resultant solution to an excess of toluene. The precipitated polymer was washed first with toluene, then with isomeric hexanes and finally dried in a vacuum oven for 24–48 hours at 80°–84° C. The typical product was a flaky or fibrous vanilla-colored solid.

The molecular weight of the solid material was determined in DMF (as 0.5% solution) at 90° C. using u-Styragel ® columns having pore sizes of $10^3$, $10^4$, and $10^5$ angstroms and polystyrene standards with a refractive index detector. The values for the weight average molecular weight (Mw), the number average molecular weight (Mn) and Mw/Mn are recorded in Table 1, together with the identification of the sulfonimidate used as the monomer. Some of the polymers were analyzed using thermogravimetric analysis under a helium atmosphere and a temperature increase rate of 10° C./minute. The temperature at which a 10% weight loss, based on initial polymer weight, was observed is recorded in Table 1 under the heading "TGA Temp.".

precursors 8aa and 8ba were heated together in a sealed ampoule and the polymer obtained after condensation had proceeded to about 76% of completion was purified once from N,N-dimethylformamide (solvent)/water (non-solvent) and once from $CH_2Cl_2$ (solvent)/hexane (non-solvent).

Analysis by GPC revealed Mw=17,785 and Mn=2,380. The polymer exhibited a Tg at 71° C. by differential scanning calorimetry (DSC) and a 10% weight loss at 279° C. under helium by thermogravimetric analysis (TGA). Proton NMR analysis showed a molar ratio of methyl to phenyl radicals of about 1:1.2.

Synthesis of Poly(4-fluorophenyloxothiazene) From Sulfonimidate 8cb

The polymerization of the sulfonimidate was conducted as described in the general procedure using no catalyst and a heating period of 243 hours. The weight of the silyl ether produced as a by-product of the polymerization indicated a 52% conversion of the sulfonimidate. The crude polymer was washed several times with a mixture of isomeric hexanes and then dried under reduced pressure for two hours. The polymer was then dissolved in 4–5 ml of N,N-dimethylformamide and precipitated into an excess of cold distilled water. The recovered polymer was then washed first with water followed by a washing with a 1:1 weight ratio mixture of 2-propanol and water and finally dried under reduced pressure at a temperature of 85° C. for 22 hours.

The glass transition temperature of the polymer, determined using differential scannining calorimetry, was 86° to 87° C. The polymer exhibited a 10% weight loss, measured using thermogravimetric analysis under helium with a heating rate of 10° C. per minute to a final temperature of 285° C. The polymer had a bimodal molecular weight distribution (Fraction 1: $M_w$=539,000, DP=3433, polydispersity=1.4; Fraction 2: $M_w$=42,700, DP=272 and polydispersity=1.2).

That which is claimed is:

1. A method for preparing a N-triorganosilylsulfonimidoyl halide represented by the formula $R^2_3SiN=S(O)(R^1)X$, said method comprising reacting a N-triorganosilyl sulfonamide corresponding to the formula $R^1SO_2N(H)_n(SiR^2_3)_{(2-n)}$ with a dihalophosphorane

TABLE 1

| Monomer | Catalyst[8] | Time (Hrs.) | % Yield | Mw | Mn | Mw/Mn | TGA Temp. |
|---|---|---|---|---|---|---|---|
| 8 ab | AlCl₃ | 100 | 69 | 284,907 | 13,770 | 20.7 | ND |
| 8 ab | AlCl₃ | 144 | 82 | 192,607 | 9,429 | 20.4 | 258 |
| 8 ab | BF₃.Et₂O[1] | 144 | 62 | 478,816 | 52,526 | 9.1 | 272 |
| 8 ab | KF/Crown[2] | 144 | 83 | 175,461 | 23,079 | 7.6 | ND |
| 8 ab | LiOPh[3] | 144 | 46 | 286,443 | 17,998 | 15.9 | 276 |
| 8 ab | TASF[4] | 144 | 58 | 374,937 | 33,246 | 11.3 | ND |
| 8 ab | None | 144 | 39 | 481,123 | 34,535 | 12.9 | ND |
| 8 ab | Sn(oct)₂[5] | 144 | 69 | 427,664 | 30,325 | 14.1 | ND |
| 8 ab | WCl₆ | 144 | 97 | 196,815 | 7,403 | 26.6 | ND |
| 8 bb[6] | None | 144 | 32 | 194,614 | 138,116 | 1.4 | ND |
|  |  |  |  | 14,110 | 12,242 | 1.2 |  |
| 8 bb[7] | KF/Crown[2] | 144 | 46–50 | 66,261 | 17,484 | 3.8[8] | ND |

Notes
[1]Boron trifluoride etherate
[2]A mixture of potassium fluoride and 18-crown-6 ether in a 1:1 mole ratio
[3]Ph = Phenyl
[4]TASF = Tris(dimethylamino)trimethylsilyl sulfur difluoride
[5]Stannous octoate
[6]The molecular weight distribution was distinctly bimodal and was analyzed as two peaks.
[7]The molecular weight distribution was bimodal and analyzed as a single peak.
[8]The catalyst concentration was 0.05 mole percent, based on monomer, for all catalyzed polymerizations.

Synthesis of Poly(Methyl-co-Phenyloxothiazene) Iab

Copolymer Iab was prepared under the same conditions described for homopolymers Ia and Ib. The two corresponding to the formula $R^3_3PX_2$, where $R^1$ is selected from the group consisting of monovalent hydrocarbon and monovalent substituted hydrocarbon radicals and heterocyclic radicals where the hetero atom is oxygen, sulfur or tertiary nitrogen, $R^2$ is selected from the group consisting of monovalent hydrocarbon and monovalent substituted hydrocarbon radicals, and n is 0 or 1, where $R^3$ represents an aryl or substituted aryl radical and X is chlorine or bromine, and isolating said N-triorganosilyl-sulfonimidoyl halide.

2. A method according to claim 1 where $R^1$ is selected from the group consisting of alkyl containing from 1 to 20 carbon atoms, substituted alkyl containing from 1 to 20 carbon atoms, aryl, substituted aryl, alkaryl and aralkenyl, $R^2$ is selected from the group consisting of alkyl containing from 1 to 4 carbon atoms, 2-perfluoroalkylethyl and phenyl, $R^3$ is phenyl, n is 1, and said reaction is conducted at a temperature of from $-78°$ to $+40°$ C.

3. A method according to claim 2 where $R^1$ is selected from the group consisting of alkyl containing from 1 to 4 carbon atoms, halogenated alkyl containing from 1 to 4 carbon atoms, beta-styryl, phenyl, chlorinated phenyl, brominated phenyl and fluorinated phenyl.

4. A method according to claim 3 where $R^1$ is methyl, ethyl, 3-chloropropyl, phenyl, 4-fluorophenyl or beta-styryl, $R^2$ represents an alkyl radical containing from 1 to 4 carbon atoms and $R^3$ is phenyl.

5. A method according to claim 4 where said halide is converted to the corresponding sulfonimidate by reaction with an alcohol or a phenol.

6. A method according to claim 1 where said N-triorganosilyl sulfonamide is prepared by reacting (a) a hexavalent sulfur compound selected from the group consisting of organosulfonyl chlorides represented by the formula $R^1SO_2Cl$ and organosulfonic anhydrides of the formula $(R^1SO_2)_2O$ with (b) a hexaorganodisilazane of the formula $(R^2{}_3Si)_2NH$.

7. A method according to claim 6 where $R^1$ is selected from the group consisting of alkyl containing from 1 to 20 carbon atoms, substituted alkyl containing from 1 to 20 carbon atoms, aryl, substituted aryl, alkaryl and aralkenyl, $R^2$ is selected from the group consisting of alkyl containing from 1 to 4 carbon atoms, 2-perfluoroalkylethyl and phenyl, $R^3$ is a phenyl radical, and n is 1.

8. A method according to claim 7 where $R^1$ represents alkyl containing from one to four carbon atoms, phenyl, chlorinated phenyl, fluorinated phenyl or beta-styryl, and $R^2$ represents methyl.

9. A method according to claim 1 where an N,N-bis(-triorganosilyl)sulfonamide is prepared by reacting a sulfonamide of the formula $R^1SO_2NH_2$ with the combination of a triorganohalosilane of the formula $R^2{}_3SiCl$ and an acid acceptor.

10. A method according to claim 9 where $R^1$ is selected from the group consisting of alkyl containing from 1 to 20 carbon atoms, substituted alkyl containing from 1 to 20 carbon atoms, aryl, substituted aryl, alkaryl and aralkenyl, $R^2$ is selected from the group consisting of alkyl containing from 1 to 4 carbon atoms, 2-perfluoroalkylethyl and phenyl, and $R^3$ is phenyl.

11. A method according to claim 10 where $R^1$ represents alkyl containing from one to four carbon atoms, phenyl, chlorinated phenyl, fluorinated phenyl or beta-styryl, and $R^2$ represents methyl.

* * * * *